(12) United States Patent
Johnson et al.

(10) Patent No.: US 11,147,763 B2
(45) Date of Patent: Oct. 19, 2021

(54) VAGINAL RING WITH VISUAL INDICATION OF USE

(71) Applicant: RESEARCH TRIANGLE INSTITUTE, Research Triangle Park, NC (US)

(72) Inventors: Leah Marie Johnson, Durham, NC (US); Stephanie Lynn Swarner, Cary, NC (US); Ginger Denison Rothrock, Cary, NC (US); Ariane Van Der Straten Ponthoz, Kensington, CA (US); Brian Rhys Stoner, Chapel Hill, NC (US)

(73) Assignee: RESEARCH TRIANGLE INSTITUTE, Research Triangle Park, NC (US)

(*) Notice: Subject to any disclaimer, the term of this patent is extended or adjusted under 35 U.S.C. 154(b) by 0 days.

(21) Appl. No.: 15/770,722

(22) PCT Filed: Oct. 25, 2016

(86) PCT No.: PCT/US2016/058566
§ 371 (c)(1),
(2) Date: Apr. 24, 2018

(87) PCT Pub. No.: WO2017/074886
PCT Pub. Date: May 4, 2017

(65) Prior Publication Data
US 2019/0070104 A1    Mar. 7, 2019

Related U.S. Application Data

(60) Provisional application No. 62/247,253, filed on Oct. 28, 2015.

(51) Int. Cl.
*A61K 9/00* (2006.01)
*A61F 6/08* (2006.01)
*A61M 31/00* (2006.01)

(52) U.S. Cl.
CPC .............. *A61K 9/0036* (2013.01); *A61F 6/08* (2013.01); *A61M 31/002* (2013.01)

(58) Field of Classification Search
CPC ....... A61K 9/0036; A61F 6/08; A61M 31/002
See application file for complete search history.

(56) References Cited

U.S. PATENT DOCUMENTS 8,404,272 B2    3/2013    Shalaby
2005/0250620 A1  11/2005   Minuto et al.
(Continued)

FOREIGN PATENT DOCUMENTS

WO    2007103474 A2    9/2007

OTHER PUBLICATIONS

Boyd, P., et al., "A Temperature-Monitoring Vaginal Ring for Measuring Adherence", "PLoS One", May 12, 2015, Page(s) DOI:10.1371/journal.pone.0125682, vol. 10, No. 5, Publisher: Queen's University Belfast.

(Continued)

*Primary Examiner* — Robert A Wax
*Assistant Examiner* — Quanglong N Truong
(74) *Attorney, Agent, or Firm* — Hultquist, PLLC; Steven J. Hultquist (57) ABSTRACT

The disclosure provides biomedical devices comprising indicator agents sensitive to the environment of use, methods of using same to enhance adherence to a treatment or usage regimen, and systems for monitoring compliance of use of the biomedical device. The biomedical device may be an intravaginal ring comprised of biocompatible polymeric material having indicator agent incorporated therein capable of producing a detectable change in response to a stimulus within the vaginal environment.

23 Claims, 11 Drawing Sheets
(10 of 11 Drawing Sheet(s) Filed in Color)

(56) References Cited

U.S. PATENT DOCUMENTS

| | | | |
|---|---|---|---|
| 2012/0093911 A1* | 4/2012 | Malcolm | A61K 9/0036 |
| | | | 424/433 |
| 2012/0259167 A1* | 10/2012 | Karapasha | A61F 2/005 |
| | | | 600/30 |
| 2013/0240804 A1 | 9/2013 | Pagba et al. | |
| 2014/0129253 A1 | 5/2014 | Hanina et al. | |
| 2014/0209100 A1* | 7/2014 | Kiser | A61K 31/522 |
| | | | 128/832 |
| 2015/0050196 A1* | 2/2015 | Chan | G01N 31/229 |
| | | | 422/426 |

OTHER PUBLICATIONS

Friend, D., "Intravaginal rings: controlled release systems for contraception and prevention of transmission of sexually transmitted infections", "Drug Delivery and Translation Research", Jun. 2011, pp. 185-193, vol. 1, No. 3, Publisher: Controlled Release Society.
Malcolm, R., et al., "Vaginal rings for delivery of HIV mirobicides", "International Journal of Women's Health", 2012, pp. 595-605, No. 4, Publisher: Dovepress.
Martin, L., et al., "The challenge of patient adherence", "Therapeutics and Clinical Risk Management", 2005, pp. 189-199, vol. 1, No. 3, Publisher: Dove Medical Press Limited.
MCConville, C., "The Use of Localised Vaginal Drug Delivery as Part of a Neoadjuvant Chemotherapy Strategy in the Treatment of Cervical Cancer", "Gynecology and Obstetrics Research", Mar. 3, 2015, pp. 26-28, vol. 2, No. 1, Publisher: Openventio Publishers.
Muula, A., "HIV Infection and AIDS Among Young Women in South Africa", "Croat Med J.", 2008, pp. 423-435, vol. 49, Publisher: www.cmj.hr.
Shisana, O., et al., "South African National HIV Prevalence, HIV Incidence, Behaviour and Communication Survey, 2005", "HSRC Report", 2005, Page(s) www.hsrcpress.ac.za, Publisher: HSRC Press.
Shisana, O., et al., "South African National HIV Prevalence, Incidence and Behaviour Survey, 2012", "HSRC Report", 2014, Page(s) www.hsrcpress.ac.za, Publisher: HSRC Press.
"Global Report UNAIDS report on the global AIDS epidemic 2013", "Joint United Nations Programme on HIV/AIDS (UNAIDS)", 2013, Publisher: World Health Organization.

* cited by examiner

VAGINAL RING WITH VISUAL INDICATION OF USE

CROSS-REFERENCE TO RELATED APPLICATIONS

This is a U.S. national phase under the provisions of 35 U.S.C. § 371 of International Patent Application No. PCT/US16/58566 filed Oct. 25, 2016, which in turn claims benefit of priority to U.S. Provisional Application No. 62/247,253 filed Oct. 28, 2015. The disclosures of such international patent application and provisional application are hereby incorporated herein by reference in their respective entireties, for all purposes.

FIELD

The present disclosure relates to polymer-based biomedical devices comprising indicator agents sensitive to the environment of use, methods of using same to enhance adherence to a treatment or usage regimen, and systems for monitoring compliance of use of the polymer-based biomedical device.

The polymer-based biomedical device may be an intravaginal ring comprised of polymeric material having indicator agent incorporated therein capable of producing a detectable change in response to a stimulus within the vaginal environment.

DESCRIPTION OF THE RELATED ART

Intravaginal rings are a dosage or drug delivery form used to locally or systemically deliver pharmaceutically useful or other bioactive agents into the vagina. Such dosage form may be capable of releasing the bioactive agent or agents over an extended period of time, depending on requirements of the agent and the condition treated.

Intravaginal rings are typically torus-shaped, flexible devices made of biocompatible material, such as silicone, elastomeric material, or thermoplastic material, generally incorporating one or more bioactive agents, such as drugs. Intravaginal rings usually are formulated as matrix or reservoir devices, but other structures may be used.

Intravaginal rings can offer unique advantages to combat various infections, such as HIV, by delivering drug continuously over the course of an extended period, e.g., a month. The simple regimen and low user burden of intravaginal rings may offer protection against HIV infection, for example. For instance, intravaginal rings do not depend on administering drug before intercourse (e.g., vaginal gels) or performing a daily action (e.g., daily pill). These advantages of intravaginal rings are apparent from the multiple vaginal rings clinical trials currently underway in Sub-Saharan Africa (e.g., ASPIRE, The Ring Study), where an estimated 70% of all new HIV infections occur per year.

The success of intravaginal rings for pre-exposure prophylaxis (PrEP) delivery critically depends on understanding women's adherence, or the extent women comply with medical instruction. Currently, the adherence of vaginal rings is primarily determined via patient self-report (i.e., questionnaires). This subjective approach is inherently error-prone with the potential for incorrect reports or falsification. For example, adherence levels in the ASPIRE and The Ring Study have apparently been challenging at some locations or under some circumstances, as revealed by anecdotal reports. For example, women from developing countries often remove their vaginal ring during the month because of opposition from their sexual partner or for other reasons. Before their monthly visit to medical caregivers, the women will reinsert the device. Moreover, many women incorrectly use the device by forgetting to reinsert for long periods of time. For this reason, medical practitioners may unknowingly generate erroneous interpretations of ring efficacy. Because intravaginal rings are a promising delivery vehicle for HIV drugs, clinicians must conclusively know the level of compliance to correctly assess the effectiveness of the devices. Thus, determining adherence in clinical trials is an important issue in demonstrating efficacy since product efficacy cannot be measured if there is low user adherence.

In addition to use with HIV prophylaxis or treatment, there are other uses for intravaginal rings which require monitoring and good adherence for effective administration of a bioactive agent. Monitoring and compliance with use may be important for other biomedical devices, as well.

Accordingly, there is a need in the art for devices and methods capable of supporting the monitoring of usage and adherence to medical protocols by patients during use of biomedical devices such as intravaginal rings.

SUMMARY

The present disclosure relates to intravaginal rings having indicator agent incorporated therein capable of producing a detectable change in response to a stimulus within the vaginal environment.

In one aspect, the disclosure relates to an intravaginal ring for delivery of bioactive agent to a vaginal environment, the intravaginal ring comprising bioactive agent in a form that is delivered by the intravaginal ring to the vaginal environment when the intravaginal ring is installed in a vaginal locus; and an indicator agent which in interaction of said intravaginal ring with the vaginal environment produces a detectable change indicative of the interaction.

In another aspect, the disclosure relates to a gynecological health kit, comprising (a) a multiplicity of intravaginal rings, each comprising bioactive agent in a form that is delivered by the intravaginal ring to the vaginal environment when the intravaginal ring is installed in a vaginal locus; and an indicator agent which in interaction of said intravaginal ring with the vaginal environment produces a detectable change indicative of the interaction; and (b) a detector configured to detect the change indicative of the interaction of the intravaginal ring with the vaginal environment.

In a further aspect, the disclosure relates to a method for monitoring compliance with a medical protocol comprising delivery of a bioactive agent to a vaginal environment, said method comprising: installing, or causing to be installed, in a vaginal locus, an intravaginal ring comprising bioactive agent in a form that is delivered by the intravaginal ring to the vaginal environment when the intravaginal ring is installed in a vaginal locus; and an indicator agent which in interaction of said intravaginal ring with the vaginal environment produces a detectable change indicative of the interaction; removing the intravaginal ring form the vaginal locus; and inspecting the intravaginal ring for a detectable change.

Other aspects, features and embodiments of the invention will be more fully apparent from the ensuing disclosure and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

As used herein and in the appended claims, the singular forms "a", "and", and "the" include plural referents unless the context clearly dictates otherwise. Like numbers refer to like elements throughout.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

The present disclosure generally relates to biomedical devices, e.g., polymer-based bioactive agent delivery devices, comprising indicator agents sensitive to the environment of use. By way of example, such biomedical devices may include intravaginal rings, catheters, medical tubing, bandages and the like.

The present disclosure further relates to intravaginal rings comprised of biocompatible polymeric material having indicator agent incorporated therein capable of producing a detectable change in response to a stimulus within vaginal environments. The detectable change may be a visually perceptible color change, such as a color change visible to the human eye, a change determinable by colorimetric or spectrophotometric measurement, or other detectable change. Nonlimiting examples of detectable changes in response to a stimulus within vaginal environments include a change in the mechanical properties, the electrical conductivity, the thermal conductivity, the ionic conductivity, the density or the index of refraction of the vaginal ring material.

Thus, in one aspect, the present disclosure is directed to an intravaginal ring for delivery of bioactive agent to a vaginal environment, said intravaginal ring comprising: bioactive agent in a form that is delivered by the intravaginal ring to the vaginal environment when the intravaginal ring is installed in a vaginal locus; and an indicator agent which in interaction of said intravaginal ring with the vaginal environment produces a detectable change indicative of said interaction.

As used herein, "vaginal ring" (VR) and "intravaginal ring" (IVR) are interchangeable and have the same meaning.

One type of intravaginal ring design contains solid drug particles dispersed substantially throughout the entire polymeric matrix. Such matrix rings typically operate through a permeation mechanism wherein the release rate is dependent on one or more of the solubility of the bioactive agent in the polymer, the ability of the solvated bioactive agent to diffuse through the polymer, the loading of the bioactive agent within the intravaginal ring and the surface area of the intravaginal ring.

Another type of intravaginal ring design is a reservoir configuration wherein the bioactive agent in contained within a reservoir in the ring. Such designs provide constant daily release rates throughout the period of use, substantially conforming to "zero order" release kinetics.

The intravaginal rings of the disclosure may be either matrix or reservoir rings or other types of intravaginal rings designed for particular purposes such as rings loaded with pods containing bioactive agent or drug cores coated with bioactive agent.

The range of materials useful for the intravaginal rings of the disclosure may be constrained by the requirements for biocompatibility, flexibility and high bioactive agent permeability. The intravaginal rings according to the disclosure will comprise biocompatible materials known for or capable of use in the body. The biocompatible material of the vaginal ring preferably will not interfere with delivery of the bio active agent and will not unintentionally degrade during manufacture, transport, and usage.

The intravaginal rings of the disclosure for use in the body will be comprised of a biocompatible material, e.g., biocompatible polymeric material, such as elastomeric or thermoplastic material. The intravaginal rings may comprise a biocompatible material in and/or on which (i) the bioactive agent is present for delivery to the vaginal environment when the intravaginal ring is installed in a vaginal locus, and/or (ii) the indicator agent is present to produce the detectable change during said interaction of said intravaginal ring with the vaginal environment.

Thus, in one aspect, the bioactive agent is in, on, or both in and on the biocompatible material and the indicator agent is in, on, or both in and on the biocompatible material. By way of example, in such aspect, the bioactive agent and the indicator agent may both be comprised in a matrix of the biocompatible material. By way of a further example, in such aspect, the bioactive agent may be comprised in a matrix of the biocompatible material and the indicator agent may be on a surface of the biocompatible material. Other combinations are readily understood by those skilled in the art.

Alternatively, the bioactive agent is in, on, or both in and on the biocompatible material or the indicator agent is in, on, or both in and on the biocompatible material. By way of example, in such aspect, the bioactive agent may be present in a pod or other defined compartment within the ring and the indicator agent is incorporated in a matrix of the biocompatible material. By way of a further example, the bioactive agent may be incorporated in a matrix of the biocompatible material and the indicator is present in a defined compartment within the ring. Multiple indicator agents may be included within the same ring, in the same or different compartments, such that additional information can be gathered beyond duration of use, including vaginal health, intercourse, and pregnancy. Other combinations are readily understood by those skilled in the art.

The biocompatible material, in aspects of the disclosure, comprises a polymeric material. A variety of physiologically acceptable resins or elastomers may be suitable for making vaginal rings, including silicones such as polyorganosiloxanes, e.g., polydimethylsiloxane or a copolymer of dimethylsiloxane and methylvinylsiloxane, conventional silicone rubber, polyurethanes, SILASTIC 382 (Dow Corning), latex rubber, polyamides, polyesters, polytetrafluoroethylene, polyethylene vinyl acetate and nylon.

Thus, in one aspect, the polymeric material comprises polymer selected from the group consisting of silicones, polyorganosiloxanes, polydimethylsiloxane, dimethylsiloxane and methylvinylsiloxane copolymers, silicone rubbers, polyurethanes, latex rubber, polyamides, polyesters, polytetrafluoroethylene, polyethylene vinyl acetate, nylon, and compatible blends, mixtures, and composites of two or more of the foregoing.

Preferably, the intravaginal rings of the disclosure comprise a silicone material (e.g., poly-dimethylsiloxane), polyurethane or ethylene-vinyl-acetate (EVA). The intravaginal rings of the present disclosure more preferably contain a silicone material.

In some aspects, the vaginal rings may comprise a permeable or semi-permeable polymer or polymer surface. Such permeability allows for biological fluids in the vaginal environment to diffuse into the ring. Alternatively, such permeability may allow for an indicator agent to diffuse out of the vaginal ring.

The biocompatible material thus may be permeable to a bioactive agent for delivery thereof to a vaginal environment when the intravaginal ring is installed in a vaginal locus or, alternatively, be permeable to vaginal fluids comprising fluids in and/or secreted from the vaginal locus, for contact of the vaginal fluids with an indicator agent.

The stimulus for detectable change, such as color change, in a vaginal environment may include pH, temperature, light, biological elements such as proteins, enzymes, peptides, carbohydrates, lipids, nucleic acids, cellular structures, organelles, bacteria, viruses, yeast, sperm or other biomolecules, redox active elements, metals, ions, moisture, or chemicals associated with biofilms. By way of example, metals may include calcium, magnesium, and the like. In appropriate environments, the stimulus for color change may include conductivity, chelation, surface properties, index of refraction, or mechanical properties of the biocompatible material or indicator agent.

The indicator agent may be any agent capable of reacting to the environment in which the biomedical device is placed to effect a detectable change. By way of example, a suitable indicator agent in an intravaginal ring, in interaction of the intravaginal ring with the vaginal environment, produces a detectable change indicative of the interaction of the intravaginal ring and the vaginal environment. In aspects of the disclosure, the detectable change produced by the indicator agent in interaction of the intravaginal ring with the vaginal environment, comprises at least one change selected from the group consisting of color changes, pH changes, temperature changes, conductivity changes, mechanical properties changes, electrical properties changes, optical properties changes, chemical reaction changes, biochemical reaction changes, changes determinable by analytic procedures, changes determinable by assays, and biosensing-detectable changes.

In one aspect of the disclosure, the detectable change is the result of diffusion of biological components from the vaginal environment into the intravaginal ring. In another aspect of the disclosure, the detectable change is the result of diffusion of the indicator agent out of the intravaginal ring.

In some embodiments, the detectable change is not a change in temperature.

In aspects of the disclosure, the detectable change produced by the indicator agent in interaction of the intravaginal ring with the vaginal environment comprises a change in absorbance of incident radiation. The change may also comprise a change in absorbance of other types of radiation. Accordingly, in circumstances where a quantitative or definitive demonstration of the change is desired or required, the detectable change may be determined by methods such as colorimetric analysis or absorbance measurements.

In another embodiment, the detectable change produced by the indicator agent in interaction of the intravaginal ring with the vaginal environment, comprises a change in a mechanical property of the intravaginal ring. In preferred embodiments of the disclosure, the detectable change produced by the indicator agent in interaction of the intravaginal ring with the vaginal environment comprises a visually perceptible color change.

The indicator agent may be formulated to have a concentration profile that causes the intravaginal ring color to appear different or alter in wavelength as a function of time installed in a vaginal locus and, thus, into the vaginal environment. Thus, in such aspects, the detectable change produced by the indicator agent in interaction of the intravaginal ring with the vaginal environment is correlative with a length of time in which the intravaginal ring is installed in the vaginal locus.

In other embodiments, the concentration profile of the indicator agent may be formulated to provide temporal information regarding the number of times the intravaginal ring was removed from the vaginal locus. Such concentration profile, for example, may signify cycles between low pH and neutral pH or indicate spikes from acidic to basic pH, indicating that intercourse occurred.

Indicator agents useful for the biomedical devices of the disclosure may be pH-sensitive, chemically-sensitive or environmentally-sensitive, for example. For indicator agents which effect a visible color change, such change may be a function of time and may correspond to any of the stimulus such as pH, temperature, biological elements such as proteins, peptides, bacteria, yeast, sperm or other biomolecules, redox active elements, or chemicals associated with biofilms. Indicator agents that respond uniquely to one or more stimuli to generate a visually perceptible response as a function of time advantageously will be incorporated into the intravaginal rings of the disclosure.

pH-sensitive indicator agents may include bromocresol green, bromocresol purple, bromophenol red, methyl purple, methyl red, azolitmin, bromothymol blue, phenol red, methyl orange, congo red, methyl yellow, thymol blue, malachite green, neutral red, naphtholphthalein, cresol red, thymolphthalein, alizarine yellow R, indigo carmine, cresolphthalein, gentian violet, litmus and the like.

Chemically-sensitive indicator agents may include redox indicators, pH dependent or pH independent, calcium indicators, sodium indicators, magnesium indicators, and the like. Exemplary chemically-sensitive indicator agents may include N-phenylanthranilic acid, nitrophenanthroline, 2,2'-bipyridine, 2,2' -bipyridine, 5,6-dimethylphenanthroline, o-dianisidine, sodium diphenylamine sulfonate, diphenylbenzidine, diphenylamine, viologen, indigotrisulfonic acid, indigotetrasulfonic acid, indigo carmine, indiomono sulfonic acid, neutral red, methylene blue, thionine, sodium o-cresol indophenol, 2,6-dichlorophenol indophenol, eriochrome black T, calcein EDTA, N-[2-[(acetyloxy) methoxy]-2-oxoethyl]-N-[3-(2-benzothiazolyl)-6-[2-[2-[bis [2-[(acetyloxy)methoxy]-2-oxoethyl]amino]-5-methylphenoxy]ethoxy]-2-oxo-2H-1-benzopyran-7-yl]-glycine, 1H-Indole-6-carboxylic acid, 2-[4-[bis-(carboxymethyl)amino]-3-[2-[2-(bis-carboxymethyl)amino-5-methylphenoxy]ethoxy]phenyl]-, pentapotassium salt, 1H-Indole-6-carboxylic acid, 2-[4-[bis[2-[(acetyloxy) methoxy]-2-oxoethyl]amino]-3-[2-[2-[bis[2-[(acetyloxy) methoxy]-2-oxoetyl]amino]-5-methylphenoxyl]ethoxy]phenyl]-, (acetyloxy)methyl ester, 5-Oxazolecarboxylic acid, 2-(6-(bis(carboxymethyl)amino)-5-(2-(2-(bis(carboxymethyl)amino)-5-methylphenoxy)ethoxy)-2-benzofuranyl)-, pentapotassium salt 5-Oxazolecarboxylic acid, 2-(6-(bis(2-((acetyloxy)methoxy)-2-oxoethyl)amino)-5-(2-(bis(2-((acetyloxy)methoxy)-2-oxoethyl)amino)-5-methylphenoxy) ethoxy)-2-benzofuranyl)-, (acetyloxy)methyl ester, 1,3-Benzenedicarboxylic acid, 4,4'-[1,4,10-trioxa-7,13-diazacyclopentadecane-7,13-diylbis(5-methoxy-6,2-benzofurandiyl)]bis-, tetraammonium salt, 5-Oxazolecarboxylic acid, 2-[6-[bis(carboxymethyl)amino]-5-(carboxymethoxy)-2-benzofuranyl]-, tetrapotassium salt, Glycine, N-[2-(carboxymethoxy)-4-[[(2',7'-dichloro-3',6'-dihydroxy-3-oxospiro[isobenzofuran-1(3H),9'-[9H]xanthen]-5-yl) carbonyl]amino]phenyl]-N-(carboxymethyl), pentapotassium salt.

The biocompatible intravaginal ring material may contain one or more indicator agents sensitive to the vaginal environment that will change color either upon insertion into the vaginal locus or as a function of time the ring has been installed therein. The indicator agent(s) may be mixed within the ring, segmented within the ring or arranged to diffuse out of the ring to effect the detectable change or alteration of wavelength or color. In some aspects of the disclosure, a segment of an intravaginal ring may contain one or more indicator agent(s) sensitive to the same or different stimulus. Alternatively, a ring may contain multiple segments containing different indicator agents that trigger based on certain particular stimulus, such as ring removal or intercourse.

The indicator agents advantageously are present in the intravaginal ring in an amount such that upon placement in the vaginal locus, the indicator agent will exhibit a detectable change, such as color change, over an extended period of time, e.g., one to six months. The ability of the indicator agent to provide a detectable change over a particular period of time will be determined by the intended use of the intravaginal ring and the bioactive agents contained therein. If desired, the bioactive agent may comprise a time-release form.

The indicator agent typically will be a biocompatible dye. In aspects of the disclosure, the indicator agent will be a biocompatible dye capable of changing the color of a polymer-based biomedical device based on a stimulus in the environment of use. Such dyes include, but are not limited to, sulfonephthalein class of dyes, a rhodamine such as rhodamine-B, fluorescein or a derivative thereof, triphenylmethane dyes such as Brilliant Blue and bromocresol green, bromocresol purple, bromophenol red, and compatible combinations of two or more of the foregoing. In preferred examples, sulfonephthalein compounds are used. In some embodiments, a combination of dyes are used that enable color changes over a broad range of pH values.

In some embodiments, when the biocompatible material of the biomedical device is a silicone material, the indicator agent is not Alizarin or methyl red.

Particular combinations of biocompatible polymer and indicator agent may include biocompatible silicone material and at least one of rhodamine-B, fluorescein or a derivative thereof, Brilliant Blue, bromocresol green or bromocresol purple. Specific combinations may include, by way of example, polydimethyl siloxane (PDMS) and rhodamine-B; PDMS and fluorescein; PDMS and Rhodamine-B/Brilliant Blue; PDMS and Brilliant Blue; PDMS and bromocresol green; and PDMS and bromocresol purple; PDMS and Bromophenol Red; and PDMS and Resazurin.

The dimensions of the vaginal rings of the present disclosure can be determined by persons skilled in the art using standard techniques. In general, the vaginal ring typically has an overall diameter of about 40 mm to about 70 mm, preferably from 54 mm to 60 mm. The overall cross-sectional diameter of the ring generally ranges from about 4 mm to about 10 mm, and preferably from about 6 mm to about 9 mm.

Vaginal rings according to the disclosure may be of any shape or form useful for the intended purpose. Typically, vaginal rings are torus-shaped, flexible devices. However, other shapes or forms may be used.

The one or more bioactive ingredients can be any appropriate pharmaceutical, drug or other agent which can be delivered vaginally. Such bioactive agents include steroids, hormones, contraceptives, estrogens, progestins, selective estrogen receptor modulators (SERMs), progesterone receptor modulators (PRMs), anti-virals, anti-retrovirals (including non-nucleoside reverse transcriptase inhibitors (NNRTI)), chemotherapeutic agents such as fluorouracil, anti-fungals, anti-bacterials or anti-protozoals. The bioactive agent may be further be selected from the group consisting of anti-fungal, anti-bacterial, antiviral, antiretroviral, anti-inflammatory (steroidal and non-steroidal), antiproliferative, antineoplastic, immunosuppressing, and anesthetic agents, and combinations thereof. Preferably, the bioactive agent comprises at least one agent selected from the group consisting of contraceptive agents, microbicide agents, antiviral agents, and antibacterial agents. By way of example, the bioactive agent may be tenofovir, levonorgestrel (LNG), estrogen, combinations thereof, or the like.

An intravaginal ring according to the disclosure may contain more than one bioactive agent wherein each bioactive agent is directed to treatment or prophylaxis of a different disease or condition. An intravaginal ring according to the disclosure may also contain more than one bioactive agent wherein each bioactive agent is directed to treatment or prophylaxis of the same disease or condition. By way of example, an intravaginal ring according to the disclosure may be used to combat various infections such as sexually-transmitted infections (STI), including, but not limited to HIV or HSV-2, by delivering bioactive agent(s) continuously over the course of an extended period, such as one, two, three or more months. By way of another example, an intravaginal ring according to the disclosure may be used to prevent various infections such as sexually-transmitted infections (STI), including, but not limited to HIV or HSV-2, and/or prevent pregnancy, by delivering bioactive agent(s) continuously over the course of an extended period, such as one, two, three or more months.

By way of example, the intravaginal ring may contain both an estrogen and a progestin, or a progestin alone. Rings of this type are especially suitable for contraception. In other embodiments, the intravaginal ring may contain a microbicide alone or one or more microbicides in combination. Rings of this type are especially suitable as protection against, or for treating, for example, HIV/AIDS, HSV-2, or other STIs. In other embodiments, the intravaginal ring may contain both a progestin and a microbicide. Rings of this type are especially suitable for dual purposes in protection against HIV/AIDS, or other STIs, and for contraception. In some aspects, the intravaginal ring may use multipurpose prevention technology (MPT) to treat or prevent multiple conditions or diseases.

"Therapeutically effective amount" as used herein means the amount of bioactive agent needed to obtain the desired therapeutic effect for treatment of a disease or condition in a subject over the time period the intravaginal ring is to be used or installed in the vaginal locus. As used herein, "prophylactically effective amount" refers to the amount of bioactive agent effective to prevent development of disease or condition in the subject over the time period the intravaginal ring is to be used or installed in the vaginal locus. In one embodiment, the disease is HIV. The intravaginal rings according to the disclosure will typically contain a therapeutically effective amount of bioactive agent when treatment of a disease or condition is desired. The intravaginal rings according to the disclosure will typically contain a prophylactically effective amount of bioactive agent when prevention of a disease or condition is desired.

When the intravaginal rings are used for dual or multiple purposes, the ring may contain one or more bioactive agents in a therapeutically effective amount, one or more bioactive agents in a prophylactically effective amount, or combinations thereof.

In one aspect of the disclosure, the intravaginal rings as disclosed herein may be provided in a gynecological health kit. In such aspect, a gynecological health kit is provided, comprising: (a) a multiplicity of intravaginal rings as described herein; and (b) a detector configured to detect the change indicative of the interaction of the intravaginal ring with the vaginal environment.

The detector may include a spectrophotometer, mass spectrometer, fluorometer, luminescence spectrometer, infrared spectrometer, pH electrode, oxygen electrode, piezoelectric crystal, density meter, or durometer. In one nonlimiting example, the detector comprises a digital camera. In a preferred example, changes in the vaginal ring material resultant from use is detected by the unaided eye.

Intravaginal rings according to the disclosure may be manufactured by any method known by those skilled-in-the-art, but preferably by injection molding or extrusion, and more preferably by reaction injection molding of silicone material systems. The term "injection molding" refers to manufacturing processes for producing parts/devices from either thermoplastic or thermosetting materials using suitably designed injection molds.

In one aspect of the disclosure, the intravaginal rings of the disclosure may be used in methods for determining compliance of a subject with a medical protocol. In providing and assessing healthcare interventions, particularly in the developing world, there is a concern about the compliance of a patient with the use of intravaginal rings for therapeutic or prophylaxis treatment. For example, the medical personnel need to know if the patient removed the intravaginal ring during the time period the ring was supposed to be providing the treatment or prophylaxis.

A method for monitoring compliance with a medical protocol comprising delivery of a bioactive agent to a vaginal environment is thus provided, said method comprising: installing, or causing to be installed, in a vaginal locus, an intravaginal ring of a type as described herein; removing the intravaginal ring form the vaginal locus; and inspecting the intravaginal ring for a detectable change.

By use of such methods, compliance with a treatment regimen involving an intravaginal ring may be determined without reliance on customary subjective assessments, such as interviews. Rather, compliance with instructions and use of an intravaginal ring may be based, for example, on an easy to interpret colorimetric or visual signal change originating from the intravaginal ring. This method enables end users of heath care professions to accurately and rapidly measure the extent of intravaginal ring usage over the time period of the course of treatment or use of the ring.

In addition to providing the ability to visually assess the detectable change in the intravaginal ring, the methods of the disclosure enable the quantitative measurement of the detectable change. Such quantitative measurement may be by colorimetric analysis, absorption spectroscopy, fluorescence spectroscopy or other measurement methods known in the art. Specific methods include use of a BCA protein assay or Coomassie Blue protein assay; among others.

In one nonlimiting example, the quantitative measurement of detectable change occurs by measuring protein from the vaginal environment deposited on or within the vaginal ring. Nonlimiting examples of methods for the quantitative measurement of proteins include the Bradford Assay, the NanoOrange® Protein Assay, the EZQ™ Protein Assay, or changes in the UV-absorbance. In one nonlimiting example, the quantitative measurement of detectable change occurs by measuring nucleic acids from the vaginal environment deposited on or within the vaginal ring. Nonlimiting examples of methods for the quantitative measurement of nucleic acids include intercalating agents such as indole dyes, imidazole dyes, phenanthridine dyes, and acridine dyes. In a nonlimiting example, the detection of a biomolecule from the vaginal environment on or within the ring is detected using an antibody conjugated to a fluorescent, luminescent, or chromogenic molecule. In a further nonlimiting example, the quantitative measurement of detectable change occurs by measuring a carbohydrate from the vaginal environment deposited on or within the vaginal ring. In other nonlimiting examples, the deposition of glucose on or within the vaginal ring material is detected via fluorescence using horseradish peroxidase and glucose oxidase in the presence of Amplex red reactant.

In addition to application to intravaginal rings, other polymer-based biomedical devices comprising an indicator agent(s) may be provided. By way of example, polymeric catheters comprising an indicator agent incorporated therein capable of detectable change in response to a stimulus within the environment of use may be used to alert medical practioners of the duration of catheter usage or the possibility of bacterial or other microbes present in the catheter. In another example, polymeric bandages comprising an indicator agent incorporated therein capable of detectable change in response to a stimulus within the environment of use may be used to assess the requirement to change dressings. The indicator agent is such bandages could provide a color change to indicate the need for a dressing change.

EXAMPLES

Figure 1A:
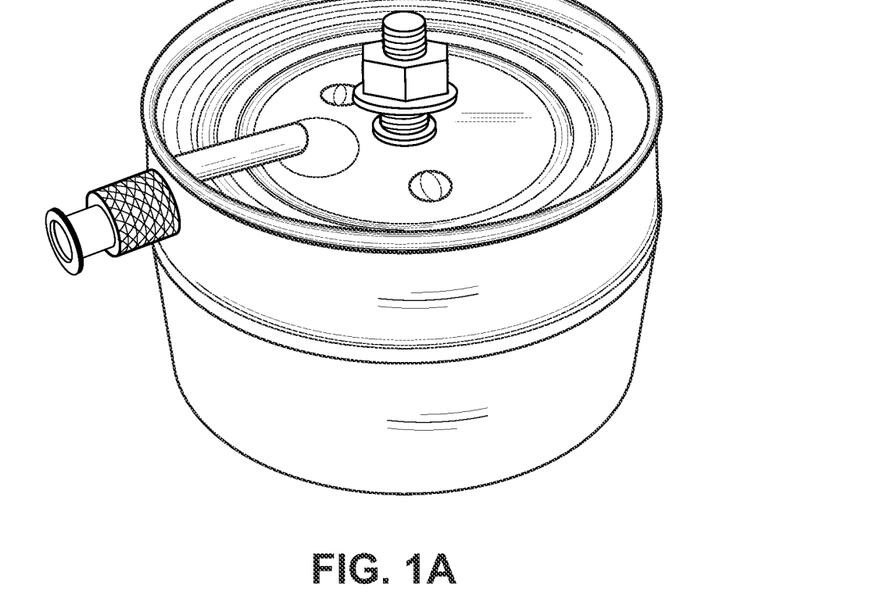
FIG. 1A is a photograph of an aluminum/epoxy mold produced to make intravaginal rings (IVRs) as shown in the photograph of FIG. 1B.
Figure 1B:
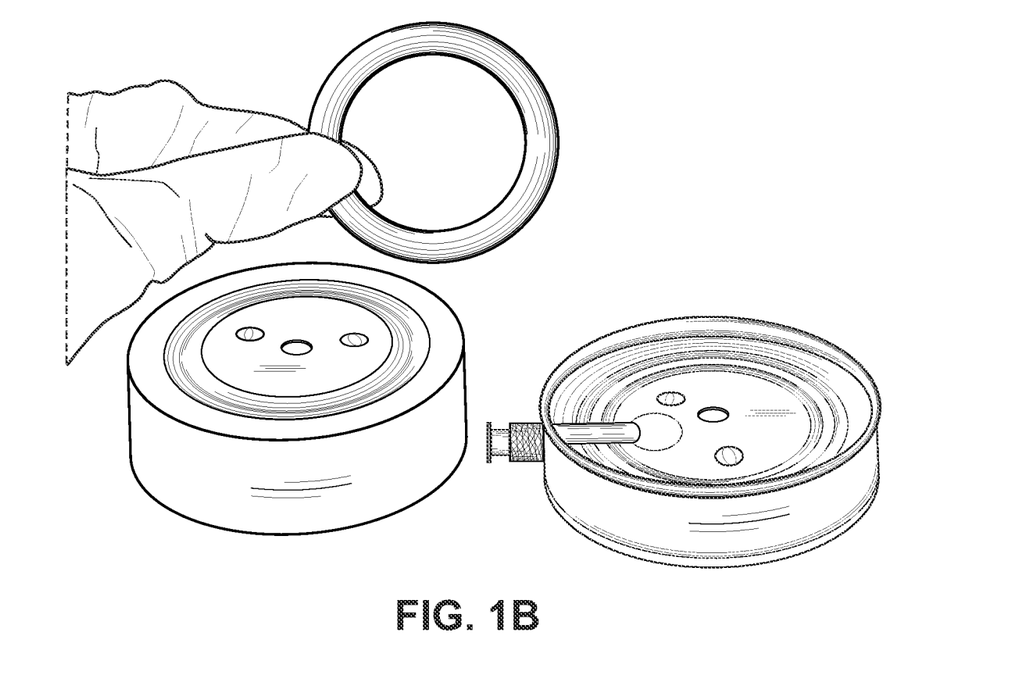
Figure 1C:
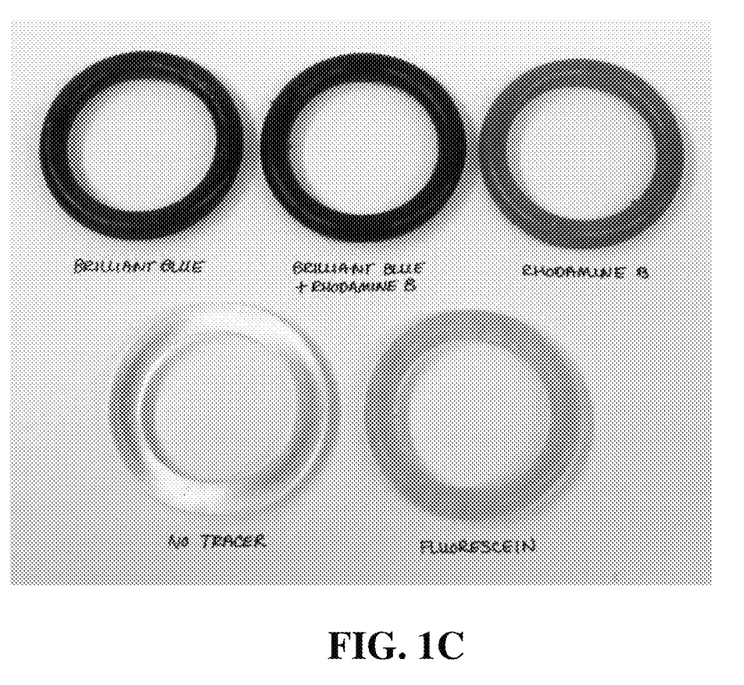
FIG. 1C is a photograph showing various IVRs which were produced using different color changing formulations.
Figure 1D:
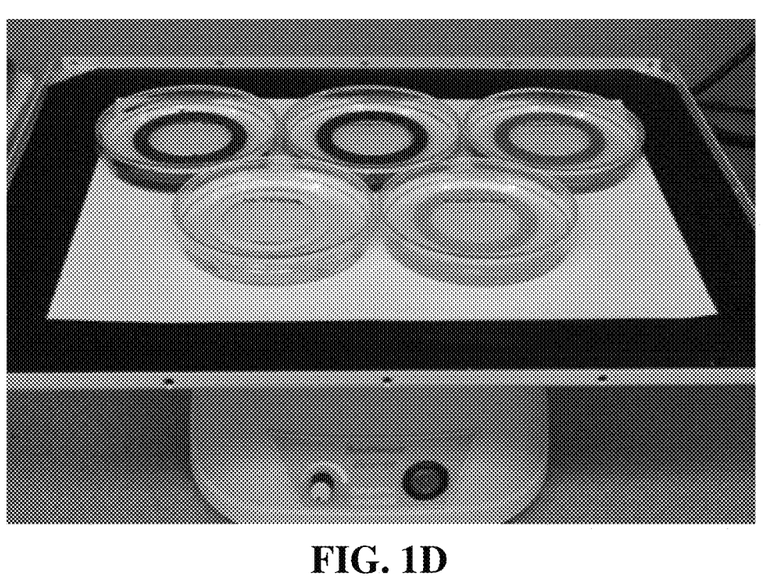
FIG. 1D is a photograph of the experimental setup used in the examples.

A custom machined aluminum/epoxy mold was designed and fabricated to match the dimensions of FDA-approved intra-vaginal ring ("IVR") devices (FIG. 1A). Silicone polymer formulations were cast into the molds and subsequently cured to produce IVRs (FIG. 1B). A variety of color changing formulations were evaluated, illustrating the potential to design the IVRs to meet clinical requirements. FIG. 1C shows the rings with the formulations including brilliant blue, brilliant blue/rhodamine-B, rhodamine B, fluorescein and no tracer. FIG. 1D is a photograph of the experimental setup used to carry out the evaluation.

Figure 2A:
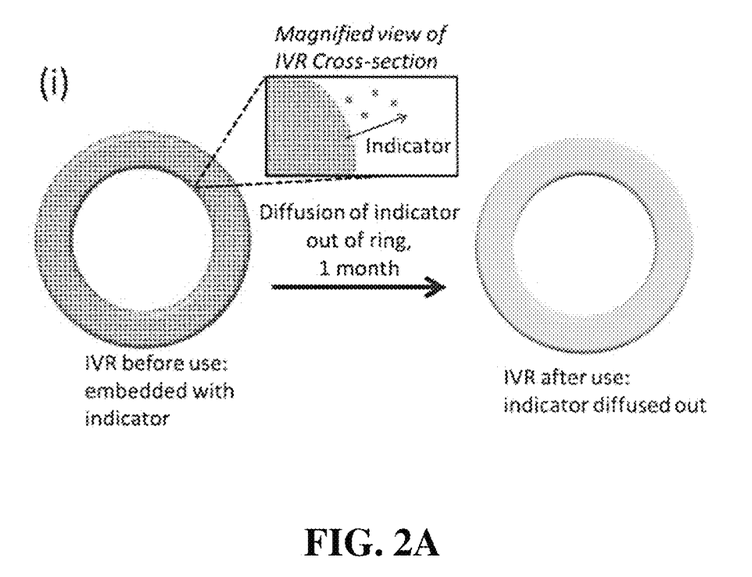
FIGS. 2A and 2B illustrate intravaginal ring color change from (i) diffusion of indicators out of the ring (FIG. 2A) or (ii) diffusion of biological constituents into the ring (FIG. 2B).
Figure 2B:
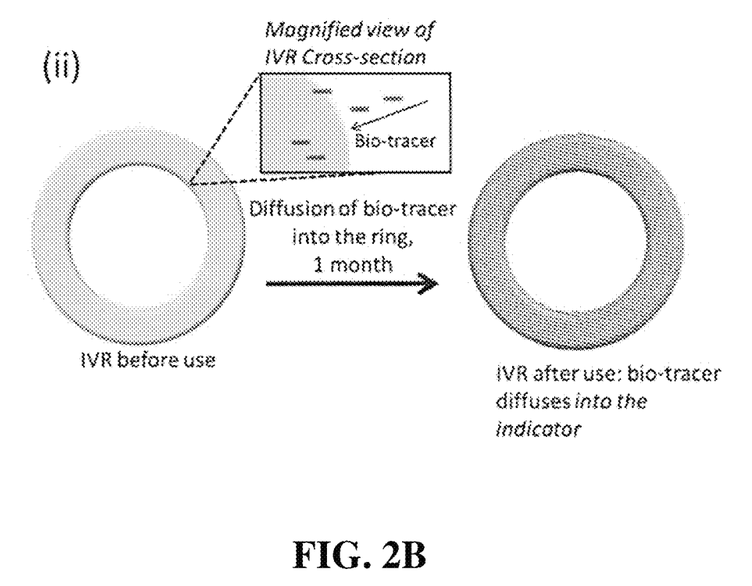

Two different approaches were tested to assess the usage of the vaginal ring (FIG. 2A and FIG. 2B). First, a system with signal change resultant of indicator diffusion (i) out of the ring was tested (FIG. 2A). The release profiles showed the ability to release colored tracers with time in simulated vaginal fluids.

The effects of biological components that diffuse (ii) into the ring were also tested (FIG. 2B).

The formulation (i.e., indicator and polymer combination) to determine the capability for enabling each of these approaches was determined as follows.

Figure 3A:
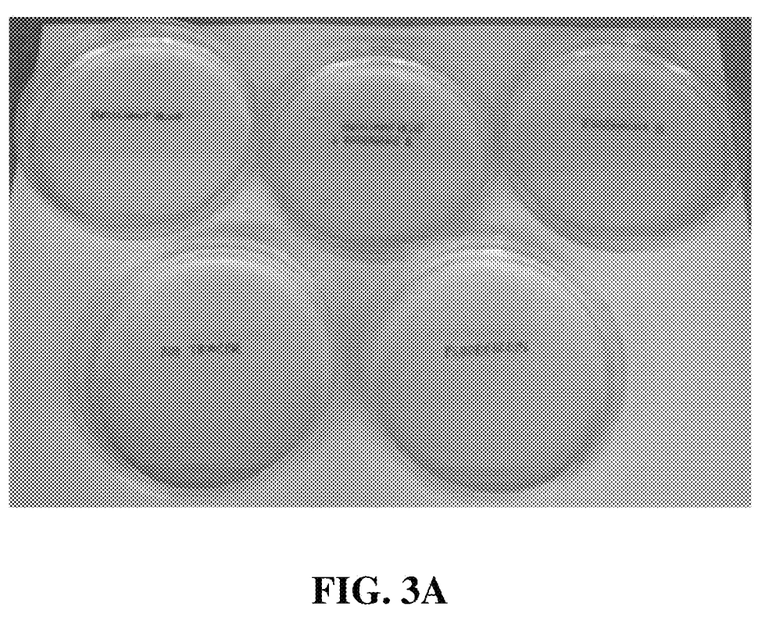
FIG. 3A is a photograph of solutions that previously contained vaginal rings, where the indicator diffused out of the vaginal ring.
Figure 3B:
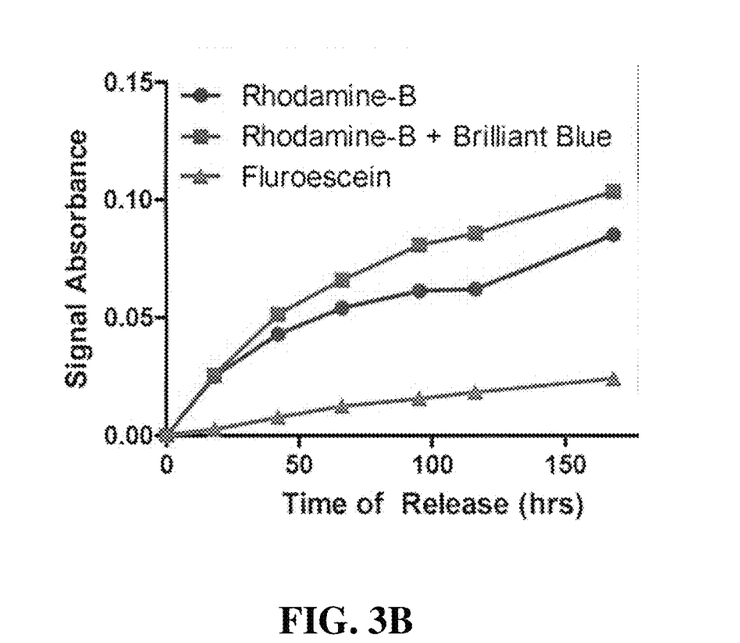
FIG. 3B is a graphical representation of the release of these indicator agents over time.

For the first approach (i.e., indicator diffusion out of the ring, FIG. 2A, i), some formulations that resulted in diffusion of tracers out of the VR (FIG. 3A) were evaluated. Results show that the vaginal ring can release indicators into the surrounding solution, thereby changing the absorbance with longer exposure of the vaginal ring in aqueous conditions. In these cases, silicone (polydimethyl siloxane, PDMS) was utilized in combination with rhodamine-B, fluorescein, and a rhodamine-B/Brilliant Blue combination. (FIG. 3A). As shown in FIG. 3B, the rhodamine-B readily released from the silicone material over the course of one week.

Figure 4:
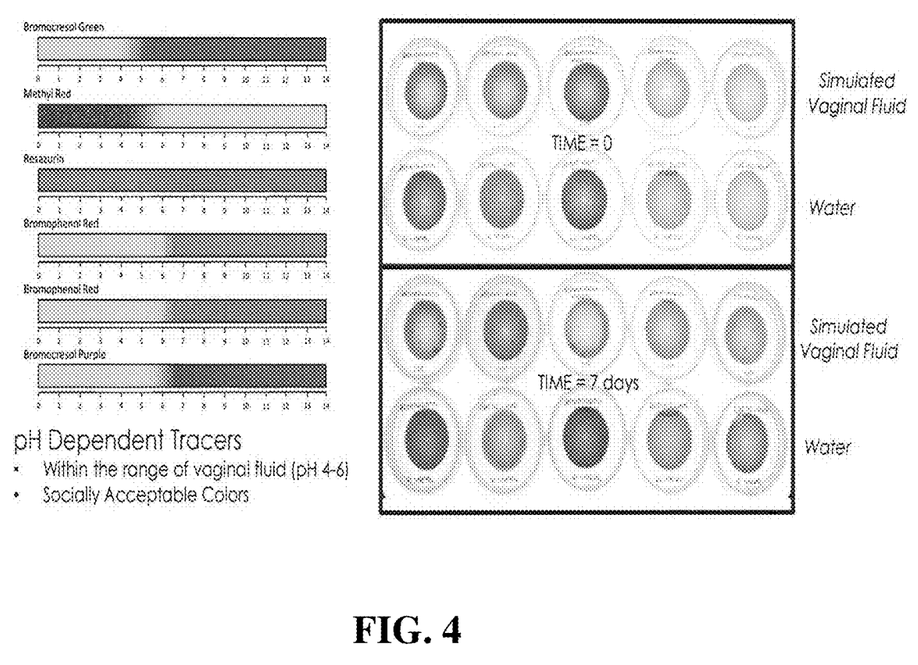
FIG. 4 illustrates the results of an evaluation of different pH indicators embedded in silicone as described in the examples.

For the second approach, research efforts focused on developing systems for analyzing biological constituents that diffuse into the ring causing a pH change (FIG. 2B, ii). To accomplish this testing strategy, a variety of pH-based color changing formulations were evaluated in biocompatible-grade silicone material. Tracers that exhibit color shifts near pH values typical within acidic vaginal environments were screened, with emphasis placed on socially acceptable colors. This material screening effort revealed promising color-changing tracers, such as Bromocresol Green and Bromocresol Purple, which display distinct color shifts within simulated vaginal fluids (FIG. 4). This material screen also facilitated the abandonment of tracers with poor performance, such as highly hydrophilic molecular families with high expulsion tendencies. For instance, Alazarin and Methyl Red tracers readily leached from the silicone material when placed into an aqueous environment.

The studies conducted have shown the ability to prepare IVRs containing pH-responsive tracers to achieve color changes resultant of biological constituents diffusing into the ring (i.e., variety of new pH-based color changing formulations in biocompatible-grade silicone material).

Figure 5:
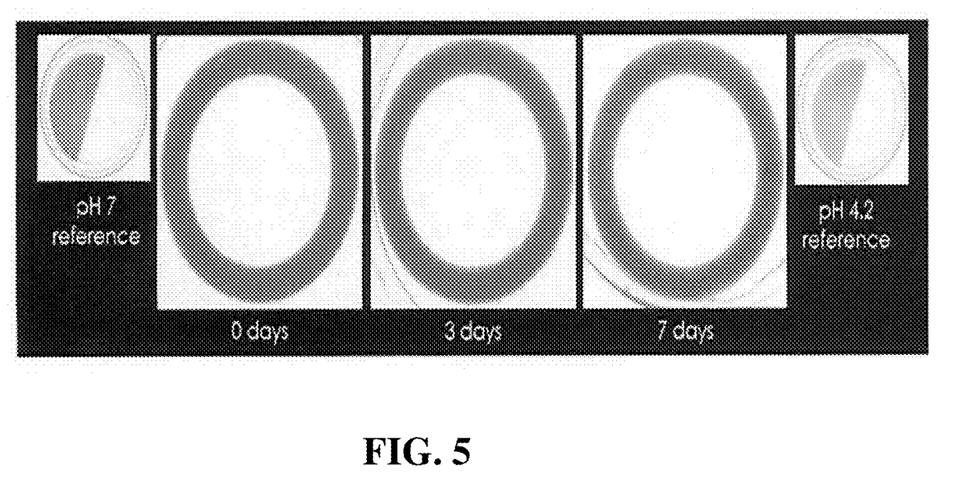
FIG. 5 is a graphic showing intravaginal rings prepared with FDA-approved silicone and embedded with bromocresol green. Intravaginal rings were placed in simulated vaginal fluid (pH=4.2) and evaluated over the course of one week.
Figure 6:
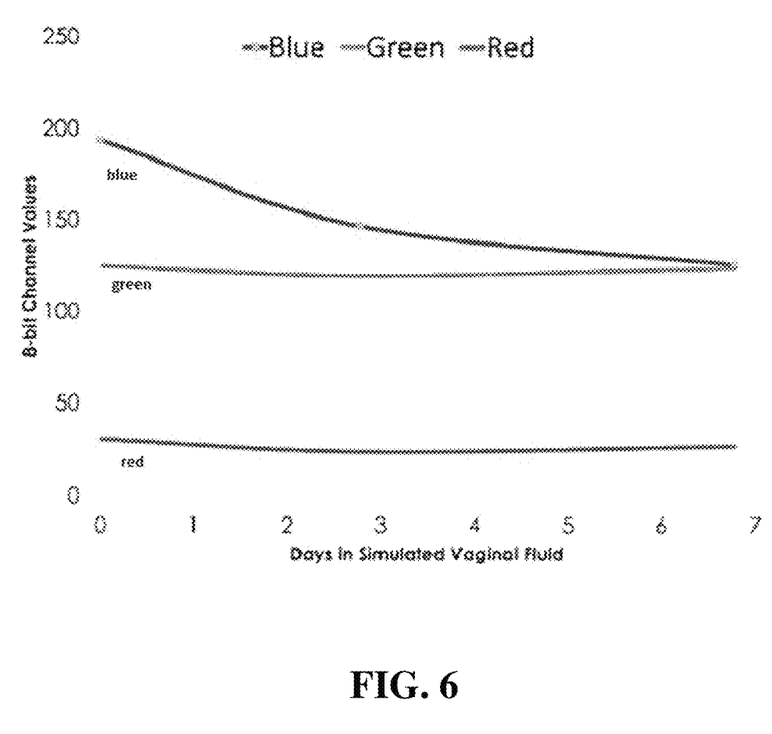
FIG. 6 is a graphical representation of the potential for quantification of vaginal rings using RGB values from digital camera images.
Figure 7:
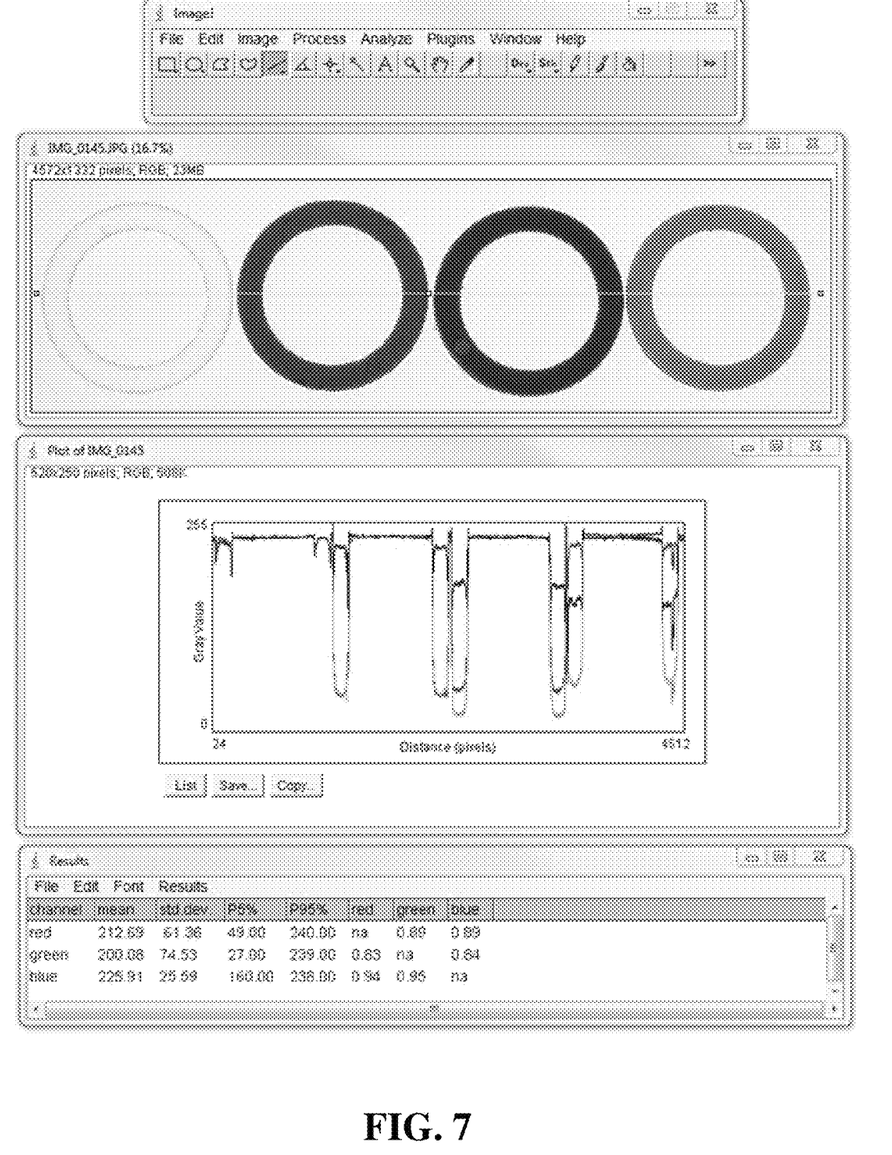
FIG. 7 is a graphical representation of the potential for quantification of vaginal rings using red, green, blue (RGB) values from digital camera images.

A custom machined aluminum/epoxy mold with FDA-compatible dimensions as described above was employed to prepare vaginal rings. Biocompatible grade (Dow Corning) silicone polymer formulations were cast into the molds and subsequently cured to produce vaginal rings embedded with the bromocresol green tracer (FIG. 5) Immersion of the vaginal rings within simulated vaginal fluid, that contained the relevant mucin protein, resulted in distinct color change over the course of seven days with a resolution of approximately seven days. The digital camera images of the rings in FIG. 6 were further evaluated using the Red, Green, Blue (RGB) color model using the Image-J open source software. The output of RGB values from an image of the VR enables assignment of quantitative values to the VR usage. An additional representation of the RGB color assignment is shown in FIG. 7.

Figure 8A:
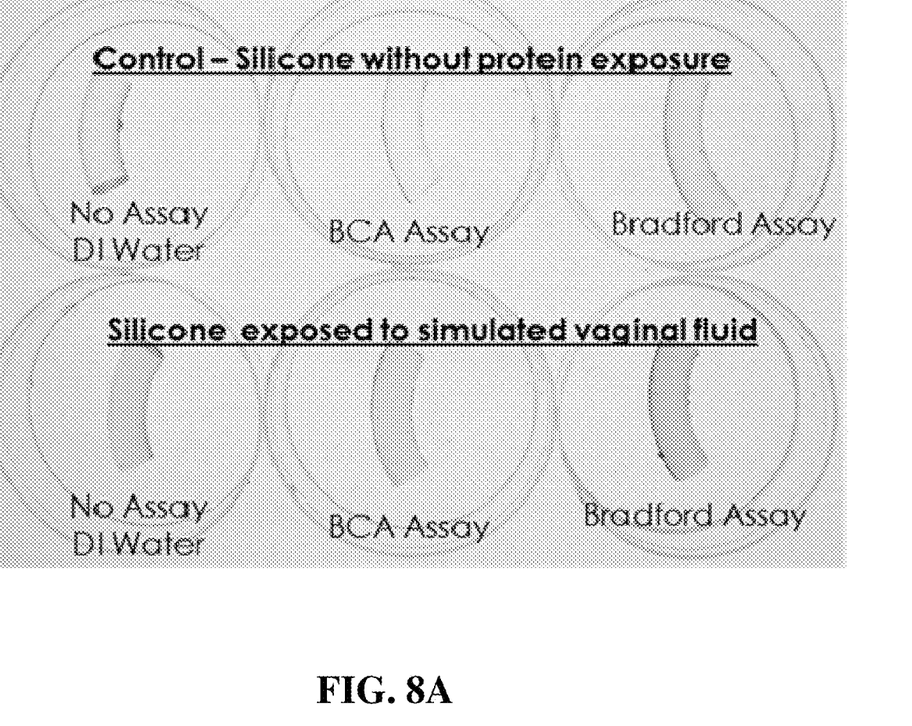
FIG. 8A shows the results of post-dip assays to evaluate ring material after exposure to simulated vaginal fluid as described in the examples.
Figure 8B:
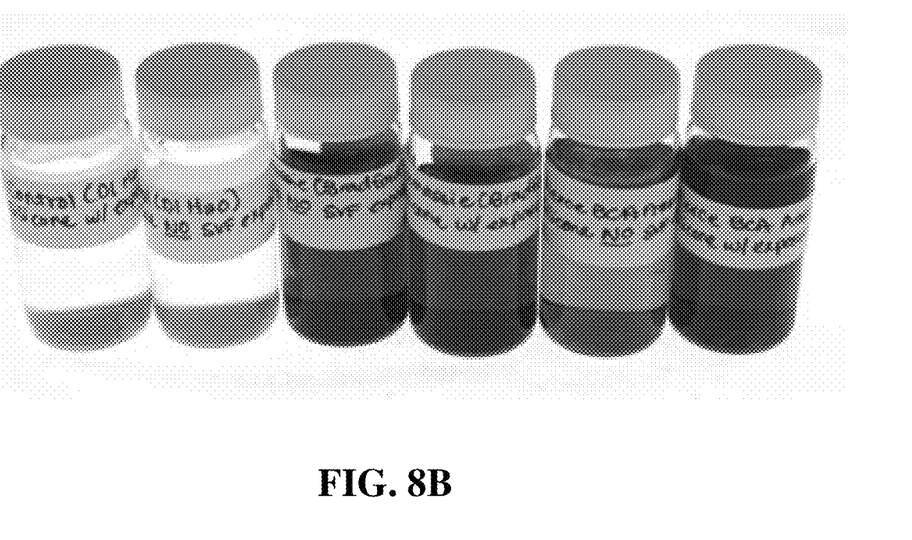
FIG. 8B shows the assay solutions 48 hours post-assay.
Figure 9:
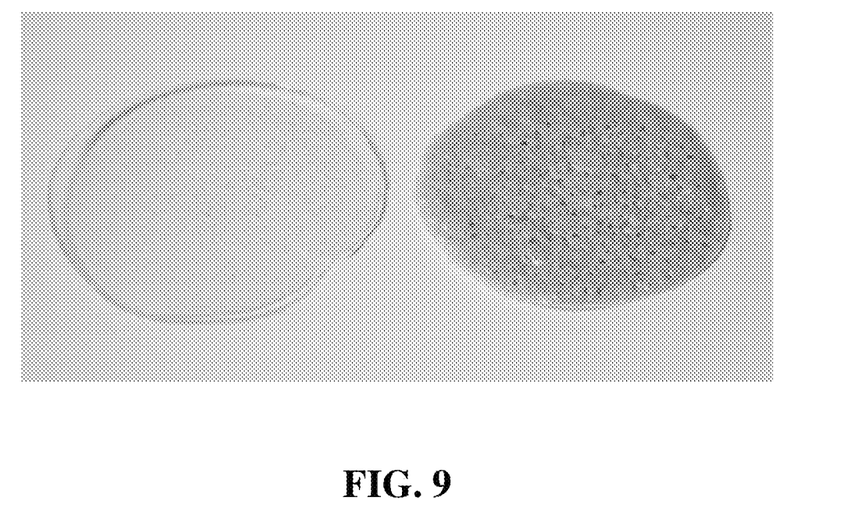
FIG. 9 shows polyurethane material without indicator (left) and polyurethane containing the bromocresol green indicator.

In addition to an immediate assessment, such as a color change, systems were evaluated that relied on a simple post-assay to evaluate diffusion of a bio-tracer into the VR. For example, two simple "post-use" dip assays were evaluated, wherein VR material was dipped into a protein stain (i.e., BCA assay or Coomassie Blue assay) after exposure to simulated vaginal fluids. Preliminary results (FIG. 8A, 8B) showed the capacity for the material to change color as a function of protein exposure. Although emphasis was placed on biocompatible silicone materials, other elastomer materials were also considered. For example, non-biomedical grade polyurethane (PU) samples were prepared and embedded with the selected Bromocresol Green. FIG. 9.

Figure 10:
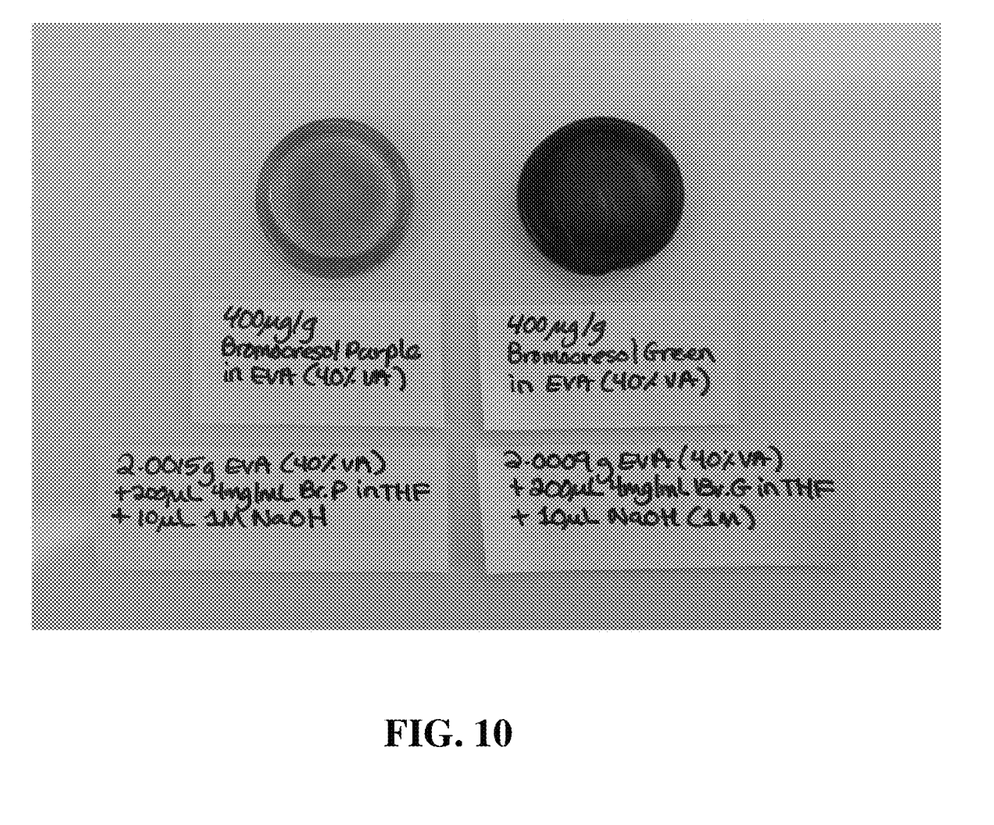
FIG. 10 shows EVA material with indicator.

FIG. 9 shows polyurethane without the bromocresol green (left) and polyurethane containing the bromocresol green indicator (right). In another example, FIG. 10 shows the ability to incorporate pH indicators into ethylene-vinyl-acetate (EVA).

Figure 11:
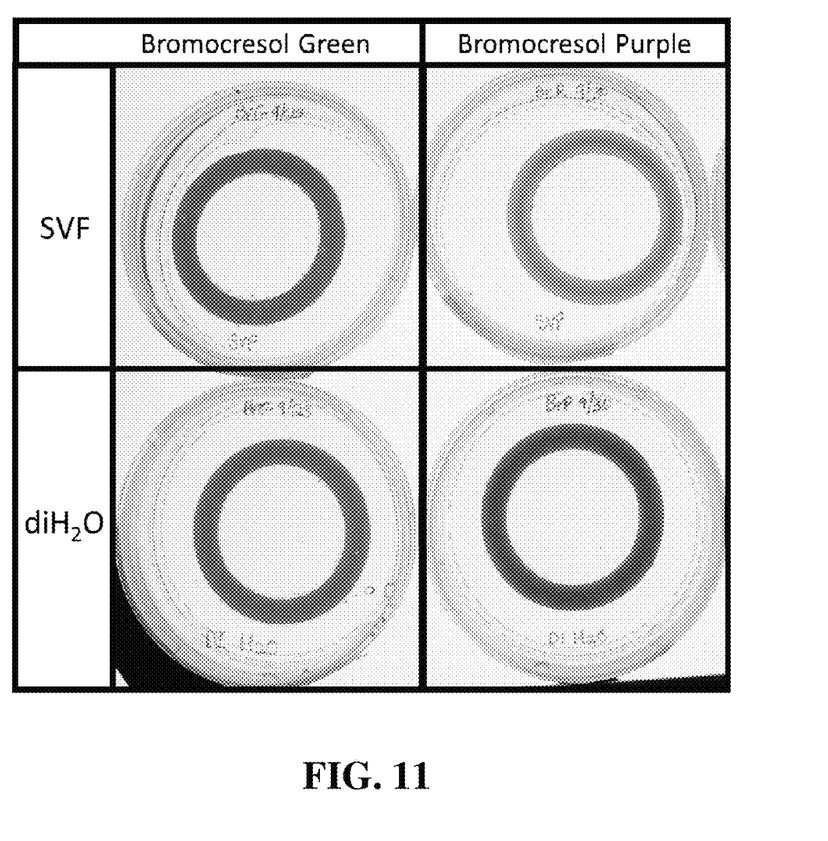
FIG. 11 shows vaginal rings containing either bromocresol green or bromocresol purple after exposure to either $diH_2O$ or simulated vaginal fluid.

FIG. 11 shows VRs that contain either bromocresol green or bromocrescol purple. The VRs were placed either in diH$_2$O or simulated vaginal fluid (pH=4.2). The VRs change color when exposed to pH=4.2.

Figure 12A:
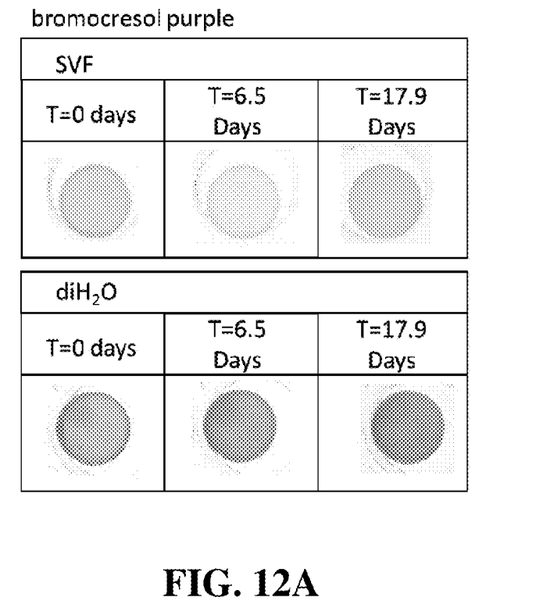
FIG. 12A shows biocompatible silicone containing bromocresol purple after immersion in $diH_2O$ or simulated vaginal fluid for different time periods.
Figure 12B:
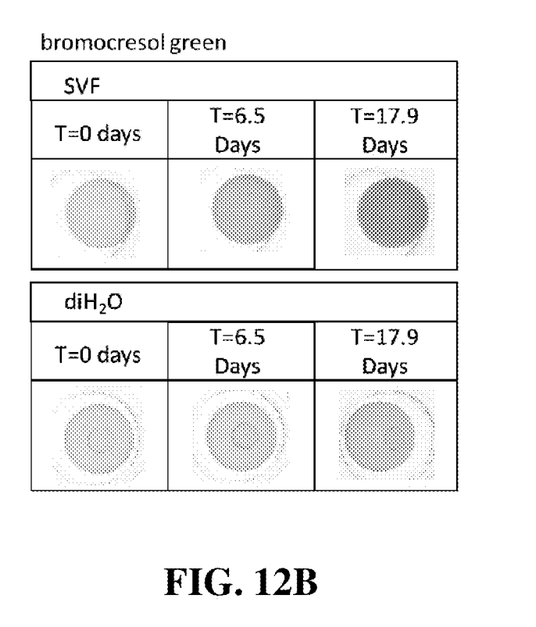
FIG. 12B shows biocompatible silicone containing bromocresol green after immersion in $diH_2O$ or simulated vaginal fluid for different time periods.

FIG. 12A shows biocompatible silicone containing bromocresol purple. FIG. 12B shows biocompatible silicone containing bromocresol green. FIG. 12A and FIG. 12B show digital camera images of the said samples after immersion in diH$_2$O or simulated vaginal fluid at (pH=4.2) for time=0, time=6.5 days, and time=17.9 days. The images show that a difference in colors is evident between samples exposed to SVF and samples exposed to diH$_2$O.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the claimed is intended to be broadly construed and interpreted, as including all such variations, modifications and alternative embodiments, within its spirit and scope.

What is claimed is:

1. An intravaginal ring for delivery of a bioactive agent to a vaginal environment, said intravaginal ring comprising:
    said bioactive agent in a form that is delivered by the intravaginal ring to the vaginal environment when the intravaginal ring is installed in a vaginal locus; and
    an indicator agent incorporated in and/or on a material of the intravaginal ring so that in interaction of said intravaginal ring with fluid in the vaginal environment, the indicator agent is contacted with the fluid to produce a detectable change in the intravaginal ring other than temperature, the detectable change being indicative of duration of contact of the intravaginal ring with the vaginal environment, as a result of said interaction.

2. The intravaginal ring of claim 1, wherein the bioactive agent comprises at least one agent selected from the group consisting of contraceptive agents, microbicide agents, antiviral agents, and antibacterial agents.

3. The intravaginal ring of claim 1, wherein the form of the bioactive agent comprises a time-release form.

4. The intravaginal ring of claim 1, wherein the detectable change indicative of the interaction of the intravaginal ring with the vaginal environment is a colorimetric change of the intravaginal ring that is correlative with a length of time during which the intravaginal ring is installed in the vaginal locus.

5. The intravaginal ring of claim 1, wherein the material of the intravaginal ring comprises a biocompatible material in and/or on which (i) the bioactive agent is present for delivery to the vaginal environment when the intravaginal ring is installed in a vaginal locus, and/or (ii) the indicator agent is present to produce the detectable change during said interaction of said intravaginal ring with the vaginal environment.

6. The intravaginal ring of claim 5, in which the biocompatible material is permeable to the bioactive agent for delivery thereof to the vaginal environment when the intravaginal ring is installed in a vaginal locus.

7. The intravaginal ring of claim 5, in which the biocompatible material is permeable to vaginal fluids comprising fluids in and/or secreted from the vaginal locus, for contact of the vaginal fluids with the indicator agent to generate the detectable change.

8. The intravaginal ring of claim 5, wherein the biocompatible material comprises a polymer selected from the group consisting of silicones, polyorganosiloxanes, polydimethylsiloxane, dimethylsiloxane and methylvinylsiloxane copolymers, silicone rubbers, polyurethanes, latex rubber, polyamides, polyesters, polytetrafluoroethylene, polyethylene vinyl acetate, nylon, and compatible blends, mixtures, and composites of two or more of the foregoing.

9. The intravaginal ring of claim 1, wherein the detectable change produced by the indicator agent in interaction of the intravaginal ring with the vaginal environment, comprises at least one change in the material of the intravaginal ring, selected from the group consisting of color changes, pH changes, conductivity changes, mechanical properties changes, electrical properties changes, optical properties changes, chemical reaction changes, biochemical reaction changes, changes determinable by analytic procedures, changes determinable by assays, and biosensing-detectable changes.

10. The intravaginal ring of claim 1, wherein the detectable change produced by the indicator agent in interaction of the intravaginal ring with the vaginal environment, comprises a visually perceptible color change.

11. The intravaginal ring of claim 1, wherein the detectable change produced by the indicator agent in interaction of the intravaginal ring with the vaginal environment, comprises a change in absorbance of incident radiation.

12. The intravaginal ring of claim 1, wherein the detectable change produced by the indicator agent in interaction of the intravaginal ring with the vaginal environment, comprises a change in a mechanical property of the intravaginal ring.

13. The intravaginal ring of claim 1, wherein the bioactive agent comprises a contraceptive agent.

14. The intravaginal ring of claim 1, wherein the bioactive agent comprises a microbicide.

15. The intravaginal ring of claim 1, wherein the bioactive agent comprises a contraceptive agent and/or an HIV/AIDS-combating microbicide.

16. The intravaginal ring of claim 1, wherein the indicator agent comprises a biocompatible dye selected from the group consisting of sulfonephthalein compounds, rhodamine, rhodamine-B, fluorescein, fluorescein derivatives, triphenylmethane dyes, Brilliant Blue, bromocresol green, bromocresol purple, bromophenol red, and compatible combinations of two or more of the foregoing.

17. The intravaginal ring of claim 1, wherein said indicator agent comprises a multiplicity of indicator materials, and wherein the intravaginal ring comprises multiple ring portions including ring portions each of which comprises differing indicator materials of said multiplicity of indicator materials.

18. The intravaginal ring of claim 17, wherein said differing indicator materials are indicatingly triggered by different stimuli.

19. The intravaginal ring of claim 1, wherein the indicator agent comprises material present or generated in the vaginal locus to which the intravaginal ring is permeable, and wherein permeated amount of said material in the intravaginal ring is indicative of the interaction of the intravaginal ring with the vaginal environment.

20. A gynecological health kit, comprising:
    (a) a multiplicity of intravaginal rings of a type as claimed in claim 1; and
    (b) a detector configured to detect the change indicative of the interaction of the intravaginal ring with the vaginal environment.

21. The intravaginal ring of claim 1, which in interaction with the fluid in the vaginal environment produces the detectable change by diffusion of the indicator agent out of the intravaginal ring.

22. The intravaginal ring of claim 1, wherein the indicator agent is formulated to produce a concentration profile providing temporal information regarding the number of times the intravaginal ring was removed from the vaginal locus.

23. The intravaginal ring of claim 22, wherein the concentration profile signifies cycles between low pH and neutral pH or spikes from acidic to basic pH.

* * * * *

UNITED STATES PATENT AND TRADEMARK OFFICE
CERTIFICATE OF CORRECTION

PATENT NO.      : 11,147,763 B2
APPLICATION NO. : 15/770722
DATED           : October 19, 2021
INVENTOR(S)     : Johnson et al.

Page 1 of 1

It is certified that error appears in the above-identified patent and that said Letters Patent is hereby corrected as shown below:

In the Specification

Column 4, Lines 55-56, "bio active" should be -- bioactive --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*